(12) United States Patent
Leutert et al.

(10) Patent No.: US 8,232,427 B2
(45) Date of Patent: Jul. 31, 2012

(54) SELECTIVE HYDROXAMATE BASED MMP INHIBITORS

(75) Inventors: Thomas Leutert, Münchenstein (CH); Jonathan E Grob, Sharon, MA (US); Ruben Alberto Tommasi, Stow, MA (US); Erin E. Pusateri, Belmont, MA (US); Ayako Honda, Quincy, MA (US)

(73) Assignee: Novartis AG, Basel (CH)

( * ) Notice: Subject to any disclaimer, the term of this patent is extended or adjusted under 35 U.S.C. 154(b) by 721 days.

(21) Appl. No.: 12/295,170

(22) PCT Filed: Mar. 27, 2007

(86) PCT No.: PCT/US2007/064972
§ 371 (c)(1),
(2), (4) Date: May 18, 2009

(87) PCT Pub. No.: WO2007/117981
PCT Pub. Date: Oct. 18, 2007

(65) Prior Publication Data
US 2009/0318511 A1 Dec. 24, 2009

Related U.S. Application Data

(60) Provisional application No. 60/786,891, filed on Mar. 29, 2006.

(51) Int. Cl.
*C07C 303/00* (2006.01)
*C07D 211/70* (2006.01)
(52) U.S. Cl. ............... 564/94; 564/84; 564/90; 564/92; 546/336
(58) Field of Classification Search .............. 546/336; 564/84, 90, 92, 94
See application file for complete search history.

(56) References Cited

U.S. PATENT DOCUMENTS

| | | | |
|---|---|---|---|
| 5,506,242 A * | 4/1996 | MacPherson et al. | 514/336 |
| 6,451,791 B1 | 9/2002 | Heintz et al. | |
| 2003/0158155 A1 | 8/2003 | Yozo et al. | |

FOREIGN PATENT DOCUMENTS
WO 03/101382 A 12/2003

OTHER PUBLICATIONS

Yusheng Xiong, et al.: "The discovery of a potent and selective lethal factor inhibitor for adjunct therapy of anthrax infection" Bioorganic & Medicinal Chemistry Letters, vol. 16, No. 4, Feb. 15, 2006, pp. 964-968. Compound 15.

S.P. Gupta, et al.: "A quantitative structure-activity relationship study on Clostridium histolyticum collagenase inhibitors: roles of electrotopological state indices" Bioorganic & Medicinal Chemistry, vol. 11, No. 14, Jul. 17, 2003, pp. 3065-3071. Compounds 1B-20, 2B-20, 3B-20.

C.T. Supuran, et al.: "Protease inhibitors: synthesis of L-alanine hydroxamate sulphonylated derivatives as inhibitors of Clostridium histolyticum collagenase" Journal of Enzyme Inhibition, vol. 15, No. 2, 2000, pp. 111-128. Compounds B20, B28.

B.W. Clare, et al.: "Protease inhibitors: synthesis of a series of bacterial collagenase inhibitors of the sulphonyl amino acyl hydroxamate type" Journal of Medicinal Chemistry, vol. 44, No. 13, May 24, 2001, pp. 2253-2258. Compounds B20, B29.

* cited by examiner

*Primary Examiner* — Jafar Parsa
(74) *Attorney, Agent, or Firm* — Sophie Binet Cross

(57) ABSTRACT

The present invention provides a compound of formula (I):

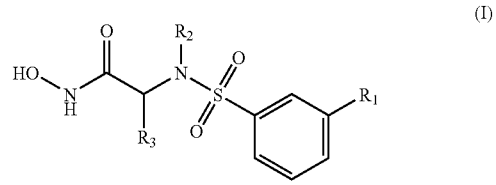

said compound is inhibitor of MMP-9, and/or MMP-12 and/or MMP-13, and thus can be employed for the treatment of a disorder or disease characterized by abnormal activity of MMP-9, and/or MMP-12 and/or MMP-13. Accordingly, the compound of formula (I) can be used in treatment of disorders or diseases mediated by MMP-9, and/or MMP-12 and/or MMP-13. Finally, the present invention also provides a pharmaceutical composition.

12 Claims, No Drawings

SELECTIVE HYDROXAMATE BASED MMP INHIBITORS

This application is the National Stage of Application No. PCT/US2007/064973, filed on Mar. 27, 2007, which claims benefit under 35 U.S.C. §119(e) of U.S. Provisional Application No. 60/786,891, filed Mar. 29, 2006, the contents of which are incorporated herein by reference in their entirety.

The present invention relates to novel compounds that are useful as inhibitors of matrix metalloproteinases such as matrix metalloproteinase 9 (MMP-9), matrix metalloproteinase 12 (MMP-12) and matrix metalloproteinase 13 (MMP-13).

In one aspect, the present invention provides a compound of formula (I)

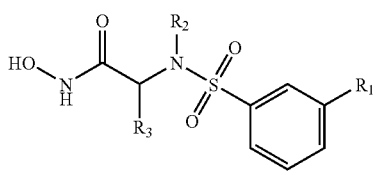

Wherein $R_1$ is cyano, alkyl, $R_4$—O—, $R_5$—C(O)NH—, or $R_6$C(O)—, wherein $R_4$, $R_5$ and $R_6$ are independently alkyl or aryl each of which is optionally substituted by one to five substituents selected from the group consisting of ($C_1$-$C_7$)alkyl, halo, hydroxyl, ($C_1$-$C_7$)alkoxy and aryl;

$R_2$ is alkyl, aryl-alkyl-, or heteroaryl-alkyl-, heterocyclyl-alkyl, or mono-alkylamino-alkyl, di-alkylamino-alkyl; and $R_3$ is alkyl; or cycloalkyl a pharmaceutically acceptable salt thereof; or an optical isomer thereof; or a mixture of optical isomers.

Preferably, the present invention provides the compound of formula (I), wherein $R_1$ is cyano, ($C_1$-$C_7$)alkyl, $R_4$—O—, $R_5$—C(O)NH—, or $R_6$C(O)—, wherein $R_4$, $R_5$ and $R_6$ are independently ($C_1$-$C_7$)alkyl, phenyl, biphenyl, naphthyl, or tetrahydronaphthyl each of which is optionally substituted by one to five substituents selected from the group consisting of ($C_1$-$C_7$)alkyl, halo, hydroxyl and ($C_1$-$C_7$)alkoxy; $R_2$ is ($C_1$-$C_7$)alkyl, ($C_6$-$C_{10}$)aryl-($C_1$-$C_7$)alkyl, (5-9 membered) heteroaryl-($C_1$-$C_7$)alkyl, (5-9 membered) heterocyclyl-($C_1$-$C_7$)alkyl, or mono-($C_1$-$C_7$)alkylamino-($C_1$-$C_7$)alkyl, or di-($C_1$-$C_7$)alkylamino-($C_1$-$C_7$)alkyl; $R_3$ is ($C_1$-$C_7$)alkyl; or a pharmaceutically acceptable salt thereof; or an optical isomer thereof; or a mixture of optical isomers.

Also more preferably, the present invention provides the compound of formula (I), wherein $R_1$ is ($C_1$-$C_7$)alkyl, $R_4$—O, $R_5$—C(O)—NH—, or $R_6$C(O)—, wherein $R_4$, $R_5$ and $R_6$ are independently ($C_1$-$C_7$)alkyl; $R_2$ is ($C_1$-$C_7$)alkyl, ($C_6$-$C_{10}$)aryl-($C_1$-$C_7$)alkyl, or (5-9 membered) heteroaryl-($C_1$-$C_7$)alkyl, (5-9 membered) heterocyclyl-($C_1$-$C_7$)alkyl, or mono-($C_1$-$C_7$)alkylamino-($C_1$-$C_7$)alkyl, or di-($C_1$-$C_7$)alkylamino-($C_1$-$C_7$)alkyl; $R_3$ is ($C_1$-$C_7$)alkyl; or a pharmaceutically acceptable salt thereof; or an optical isomer thereof; or a mixture of optical isomers.

In another embodiment, the present invention provides the compound of formula (I), wherein $R_1$ is cyano, ($C_1$-$C_7$)alkyl, amino, $R_4$—O—, ($C_1$-$C_7$)alkyl-NHC(O)—, $R_5$—C(O)NH—, $R_6$C(O)—, $R_9$—C(O)—O— or $R_{10}$—O—(O)—, wherein $R_4$, $R_6$, $R_9$, and $R_{10}$ are independently hydrogen, ($C_1$-$C_7$) alkyl, mono- or di-($C_1$-$C_7$)alkylamino or aryl each of which is optionally substituted by one to five substituents selected from the group consisting of ($C_1$-$C_7$)alkyl, halo, hydroxyl, ($C_1$-$C_7$)alkoxy and aryl;

$R_5$ is hydrogen, ($C_1$-$C_7$)alkyl or ($R_7$)($R_8$)N—;

$R_7$ and $R_8$ are independently hydrogen, ($C_1$-$C_7$)alkyl, or aryl-($C_1$-$C_7$)alkyl;

$R_2$ is hydrogen, or ($C_1$-$C_7$)alkyl which is optionally substituted by one to three substituents selected from the group consisting of ($C_1$-$C_7$)alkyl, hydroxy, aryl, heterocyclyl, heteroaryl, ($C_1$-$C_7$)alkyl-O—C(O)—, di-($C_1$-$C_7$)alkylamino-C(O)—, wherein each of aryl, heterocyclyl, and heteroaryl is further optionally substituted by ($C_1$-$C_7$)alkyl; or $R_3$ is ($C_1$-$C_7$)alkyl, or cycloalkyl;

a pharmaceutically acceptable salt thereof; or an optical isomer thereof; or a mixture of optical isomers.

Preferably, the present invention provides the compound of formula (I), wherein $R_1$ is ($C_1$-$C_7$)alkyl, $R_4$—O—, or $R_5$—C(O)NH—, wherein $R_4$ is ($C_1$-$C_7$)alkyl optionally substituted by one to three halo, $R_5$ is hydrogen or mono-($C_1$-$C_7$)-alkylamino;

$R_2$ is ($C_1$-$C_7$)alkyl optionally substituted by ($C_1$-$C_7$)alkyl-O—C(O)—, di-($C_1$-$C_7$)alkylamino, or hydroxy; or $R_2$ is aryl-($C_1$-$C_7$)alkyl-, heteroaryl-($C_1$-$C_7$)alkyl-, heterocyclyl-($C_1$-$C_7$)alkyl, wherein said heterocyclyl is optionally substituted by ($C_1$-$C_7$)alkyl; and $R_3$ is ($C_1$-$C_7$)alkyl; or a pharmaceutically acceptable salt thereof; or an optical isomer thereof; or a mixture of optical isomers.

Preferably, the present invention provides the compound of formula (I), wherein $R_1$ is ($C_1$-$C_7$)alkoxy;
$R_2$ is ($C_1$-$C_7$)alkyl;
$R_3$ is ($C_1$-$C_7$)alkyl.

Preferably, the present invention provides the compound of formula (I), wherein $R_1$ is ($C_1$-$C_7$)alkoxy;
$R_2$ is (5-9 membered) heteroaryl-($C_1$-$C_7$)alkyl;
$R_3$ is ($C_1$-$C_7$)alkyl.

In another aspect, the present invention provides the compound of formula (II)

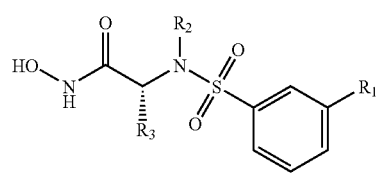

Wherein $R_1$ is cyano, alkyl, $R_4$—O—, $R_5$—C(O)NH—, or $R_6$C(O)—, wherein $R_4$, $R_5$ and $R_6$ are independently alkyl or aryl each of which is optionally substituted by one to five substituents selected from the group consisting of ($C_1$-$C_7$)alkyl, halo, hydroxyl, ($C_1$-$C_7$)alkoxy and aryl;

$R_2$ is alkyl, aryl-alkyl-, heteroaryl-alkyl-, heterocyclylalkyl, or mono-alkylamino-alkyl, di-alkylamino-alkyl; and $R_3$ is alkyl; or cycloalkyl;

a pharmaceutically acceptable salt thereof; or an optical isomer thereof; or a mixture of optical isomers.

Preferably, the present invention provides the compound of formula (II), wherein R1 is cyano, ($C_1$-$C_7$)alkyl, $R_4$—O—, $R_5$—C(O)NH—, or $R_6$C(O)—, wherein $R_4$, $R_5$ and $R_6$ are independently ($C_1$-$C_7$)alkyl, phenyl, biphenyl, naphthyl, or tetrahydronaphthyl each of which is optionally substituted by one to five substituents selected from the group consisting of $(C_1-C_7)$alkyl, halo, hydroxyl and $(C_1-C_7)$alkoxy; $R_2$ is $(C_1-C_7)$alkyl, $(C_6-C_{10})$aryl-$(C_1-C_7)$alkyl, (5-9 membered) heteroaryl-$(C_1-C_7)$alkyl, (5-9 membered) heterocyclyl-$(C_1-C_7)$alkyl, or mono-$(C_1-C_7)$alkylamino-$(C_1-C_7)$alkyl, or di-$(C_1-C_7)$alkylamino-$(C_1-C_7)$alkyl; $R_3$ is $(C_1-C_7)$alkyl; or a pharmaceutically acceptable salt thereof; or an optical isomer thereof; or a mixture of optical isomers.

Also more preferably, the present invention provides the compound of formula (II), wherein $R_1$ is $(C_1-C_7)$alkyl, $R_4$—O—, $R_5$—C(O)—NH—, or $R_6$C(O)—, wherein $R_4$, $R_5$ and $R_6$ are independently $(C1-C7)$alkyl; $R_2$ is $(C_1-C_7)$alkyl, $(C_6-C_{10})$aryl-$(C_1-C_7)$alkyl, (5-9 membered) heteroaryl-$(C_1-C_7)$alkyl, or (5-9 membered) heterocyclyl-$(C_1-C_7)$alkyl, or mono-$(C_1-C_7)$alkylamino-$(C_1-C_7)$alkyl, or di-$(C_1-C_7)$alkylamino-$(C_1-C_7)$alkyl; $R_3$ is $(C_1-C_7)$alkyl; or a pharmaceutically acceptable salt thereof; or an optical isomer thereof; or a mixture of optical isomers.

In another embodiment, the present invention provides the compound of formula (II), wherein $R_1$ is cyano, $(C_1-C_7)$alkyl, amino, $R_4$—O—, $(C_1-C_7)$alkyl-NHC(O)—, $R_5$—C(O)NH—, $R_6$C(O)—, $R_9$—C(O)—O— or $R_{10}$—O—(O)—, wherein $R_4$, $R_6$, $R_9$, and $R_{10}$ are independently hydrogen, mono- or di-$(C_1-C_7)$alkylamino, $(C_1-C_7)$alkyl or aryl each of which is optionally substituted by one to five substituents selected from the group consisting of $(C_1-C_7)$alkyl, halo, hydroxyl, $(C_1-C_7)$alkoxy and aryl;

$R_5$ is hydrogen, $(C_1-C_7)$alkyl or $(R_7)(R_8)N$—;

$R_7$ and $R_8$ are independently hydrogen, $(C_1-C_7)$alkyl, or aryl-$(C_1-C_7)$alkyl;

$R_2$ is hydrogen, $(C_1-C_7)$alkyl, which is optionally substituted by one to three substituents selected from the group consisting of $(C_1-C_7)$alkyl, hydroxy, aryl, heterocyclyl, heteroaryl, $(C_1-C_7)$alkyl-O—C(O)—, di-$(C_1-C_7)$alkylamino-C(O)—, wherein each of aryl, heterocyclyl, and heteroaryl is further optionally substituted by $(C_1-C_7)$alkyl;

$R_3$ is $(C_1-C_7)$alkyl or cycloalkyl; or a pharmaceutically acceptable salt thereof; or an optical isomer thereof; or a mixture of optical isomers.

Preferably, the present invention provides the compound of formula (II), wherein $R_1$ is $(C_1-C_7)$alkyl, $R_4$—O—, or $R_5$—C(O)NH—, wherein $R_4$ is $(C_1-C_7)$alkyl optionally substituted by one to three halo, $R_5$ is hydrogen or mono-$(C_1-C_7)$-alkylamino;

$R_2$ is $(C_1-C_7)$alkyl optionally substituted by $(C_1-C_7)$alkyl-O—C(O)—, di-$(C_1-C_7)$-alkylamino-C(O)—, hydroxy; or $R_2$ is aryl-$(C_1-C_7)$alkyl-, heteroaryl-$(C_1-C_7)$alkyl-, heterocyclyl-$(C_1-C_7)$alkyl, wherein said heterocyclyl is optionally substituted by $(C_1-C_7)$alkyl;

$R_3$ is $(C_1-C_7)$alkyl; or a pharmaceutically acceptable salt thereof; or an optical isomer thereof; or a mixture of optical isomers.

Preferably, the present invention provides the compound of formula (II), wherein $R_1$ is $(C_1-C_7)$alkoxy;

$R_2$ is $(C_1-C_7)$alkyl;

$R_3$ is $(C_1-C_7)$alkyl.

Preferably, the present invention provides the compound of formula (II), wherein $R_1$ is $(C_1-C_7)$alkoxy;

$R_2$ is (5-9 membered) heteroaryl-$(C_1-C_7)$alkyl;

$R_3$ is $(C_1-C_7)$alkyl.

In another aspect, the present invention provides a compound of formula (III)

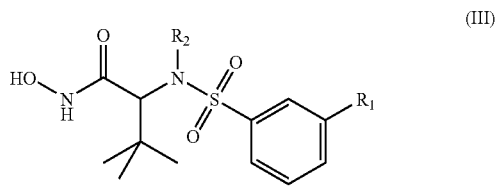

(III)

Wherein $R_1$ is nitro, cyano, halo, alkyl, $R_4$—O—, $R_5$—C(O)NH—, or $R_6$C(O)—, wherein $R_4$, $R_5$ and $R_6$ are independently alkyl or aryl each of which is optionally substituted by one to five substituents selected from the group consisting of $(C_1-C_7)$ alkyl, halo, hydroxyl, $(C_1-C_7)$alkoxy and aryl; and $R_2$ is alkyl, aryl-alkyl-, or heteroaryl-alkyl-, heterocyclylalkyl, or mono-alkylamino-alkyl, di-alkylamino-alkyl; or a pharmaceutically acceptable salt thereof; or an optical isomer thereof; or a mixture of optical isomers.

Preferably, the present invention provides the compound of formula (III), wherein R1 is nitro, cyano, halo, $(C_1-C_7)$alkyl, $R_4$—O—, $R_5$—C(O)NH—, or $R_6$C(O)—, wherein $R_4$, $R_5$ and $R_6$ are independently $(C_1-C_7)$alkyl, phenyl, biphenyl, naphthyl, or tetrahydronaphthyl each of which is optionally substituted by one to five substituents selected from the group consisting of $(C_1-C_7)$alkyl, halo, hydroxyl and $(C_1-C_7)$ alkoxy; $R_2$ is $(C_1-C_7)$alkyl, $(C_6-C_{10})$aryl-$(C_1-C_7)$alkyl, or (5-9 membered) heteroaryl-$(C_1-C_7)$alkyl, (5-9 membered) heterocyclyl-$(C_1-C_7)$alkyl, or mono-$(C_1-C_7)$alkylamino-$(C_1-C_7)$alkyl, or di-$(C_1-C_7)$alkylamino-$(C_1-C_7)$alkyl; or a pharmaceutically acceptable salt thereof; or an optical isomer thereof; or a mixture of optical isomers.

Also more preferably, the present invention provides the compound of formula (III), wherein $R_1$ is $(C_1-C_7)$alkyl, $R_4$—O, $R_5$—C(O)—NH—, or $R_6$C(O)—, wherein $R_4$, $R_5$ and $R_6$ are independently $(C_1-C_7)$alkyl; $R_2$ is $(C_1-C_7)$alkyl, (5-9 membered) heterocyclyl-$(C_1-C_7)$alkyl, or mono-$(C_1-C_7)$ alkylamino-$(C_1-C_7)$alkyl, or di-$(C_1-C_7)$alkylamino-$(C_1-C_7)$ alkyl; or a pharmaceutically acceptable salt thereof; or an optical isomer thereof; or a mixture of optical isomers.

In another embodiment, the present invention provides the compound of formula (III), wherein $R_1$ is cyano, nitro, halo, alkyl, amino, $R_4$—O—, $R_5$—C(O)NH—, or $R_6$C(O)—, wherein $R_4$, $R_5$, and $R_6$ are independently alkyl or aryl each of which is optionally substituted by one to five substituents selected from the group consisting of $(C_1-C_7)$alkyl, halo, hydroxyl, $(C_1-C_7)$alkoxy and aryl;

$R_2$ is alkyl, aryl-alkyl-, or heteroaryl-alkyl-, (5-9 membered)heterocyclyl-$(C_1-C_7)$alkyl, mono-$(C_1-C_7)$alkylamino-$(C_1-C_7)$alkyl, or di-$(C_1-C_7)$alkylamino-$(C_1-C_7)$alkyl; or a pharmaceutically acceptable salt thereof; or an optical isomer thereof; or a mixture of optical isomers.

Preferably, the present invention provides the compound of formula (III), wherein $R_1$ is nitro, cyano, halo, $(C_1-C_7)$alkyl, $R_4$—, $R_5$—C(O)NH—, or $R_6$C(O)—, wherein $R_4$, $R_5$ and $R_6$ are independently $(C_1-C_7)$alkyl, phenyl, biphenyl, naphthyl, or tetrahydronaphthyl each of which is optionally substituted by one to five substituents selected from the group consisting of $(C_1-C_7)$alkyl, halo, hydroxyl and $(C_1-C_7)$alkoxy; $R_2$ is $(C_1-C_7)$alkyl, $(C_6-C_{10})$aryl-$(C_1-C_7)$alkyl, or (5-9 membered) heteroaryl-$(C_1-C_7)$alkyl, (5-9 membered) heterocyclyl-$(C_1-C_7)$alkyl, or mono-$(C_1-C_7)$alkylamino-$(C_1-C_7)$alkyl, or di- ($C_1$-$C_7$)alkylamino-($C_1$-$C_7$)alkyl; or a pharmaceutically acceptable salt thereof; or an optical isomer thereof; or a mixture of optical isomers.

In another aspect, the present invention provides the compound of formula (IV)

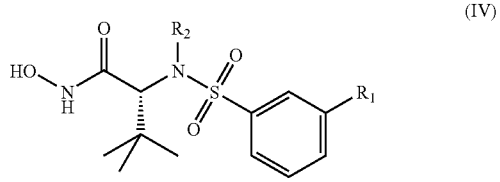

(IV)

Wherein $R_1$ is nitro cyano, halo, alkyl, $R_4$—O—, $R_5$—C(O)NH—, or $R_6$C(O)—, wherein $R_4$, $R_5$ and $R_6$ are independently alkyl or aryl each of which is optionally substituted by one to five substituents selected from the group consisting of ($C_1$-$C_7$) alkyl, halo, hydroxyl, ($C_1$-$C_7$)alkoxy and aryl; and $R_2$ is alkyl, aryl-alkyl-, or heteroaryl-alkyl-, heterocyclylalkyl, or mono-alkylamino-alkyl, di-alkylamino-alkyl; or a pharmaceutically acceptable salt thereof; or an optical isomer thereof; or a mixture of optical isomers.

Preferably, the present invention provides the compound of formula (IV), wherein $R_1$ is nitro, cyano, halo, ($C_1$-$C_7$)alkyl, $R_4$—O, $R_5$—C(O)NH—, or $R_6$C(O)—, wherein $R_4$, $R_5$ and $R_6$ are independently ($C_1$-$C_7$)alkyl, phenyl, biphenyl, naphthyl, or tetrahydronaphthyl each of which is optionally substituted by one to five substituents selected from the group consisting of ($C_1$-$C_7$)alkyl, halo, hydroxyl and ($C_1$-$C_7$) alkoxy; $R_2$ is ($C_1$-$C_7$)alkyl, ($C_6$-$C_{10}$)aryl-($C_1$-$C_7$)alkyl, or (5-9 membered) heteroaryl-($C_1$-$C_7$)alkyl, (5-9 membered) heterocyclyl-($C_1$-$C_7$)alkyl, or mono-($C_1$-$C_7$)alkylamino-($C_1$-$C_7$)alkyl, or di-($C_1$-$C_7$)alkylamino-($C_1$-$C_7$)alkyl; or a pharmaceutically acceptable salt thereof; or an optical isomer thereof; or a mixture of optical isomers.

Also more preferably, the present invention provides the compound of formula (IV), wherein $R_1$ is ($C_1$-$C_7$)alkyl, $R_4$—O, $R_5$—C(O)—NH—, or $R_6$C(O)—, wherein $R_4$, $R_5$ and $R_6$ are independently ($C_1$-$C_7$)alkyl; $R_2$ is ($C_1$-$C_7$)alkyl, (5-9 membered) heterocyclyl-($C_1$-$C_7$)alkyl, or mono-($C_1$-$C_7$) alkylamino-($C_1$-$C_7$)alkyl, or di-($C_1$-$C_7$)alkylamino-($C_1$-$C_7$) alkyl; or a pharmaceutically acceptable salt thereof; or an optical isomer thereof; or a mixture of optical isomers.

In another embodiment, the present invention provides the compound of formula (IV), wherein $R_1$ is cyano, nitro, halo, alkyl, amino, $R_4$—O—, $R_5$—C(O) NH—, or $R_6$C(O)—, wherein $R_4$, $R_5$, and $R_6$ are independently alkyl or aryl each of which is optionally substituted by one to five substituents selected from the group consisting of ($C_1$-$C_7$)alkyl, halo, hydroxyl, ($C_1$-$C_7$)alkoxy and aryl;

$R_2$ is alkyl, aryl-alkyl-, or heteroaryl-alkyl-, (5-9 membered)heterocyclyl-($C_1$-$C_7$)alkyl, mono-($C_1$-$C_7$)alkylamino-($C_1$-$C_7$)alkyl, or di-($C_1$-$C_7$)alkylamino-($C_1$-$C_7$)alkyl; or a pharmaceutically acceptable salt thereof; or an optical isomer thereof; or a mixture of optical isomers.

Preferably, the present invention provides the compound of formula (IV), wherein $R_1$ is nitro, cyano, halo, ($C_1$-$C_7$)alkyl, $R_4$—O—, $R_5$—C(O)NH—, or $R_6$C(O)—, wherein $R_4$, $R_5$ and $R_6$ are independently ($C_1$-$C_7$)alkyl, phenyl, biphenyl, naphthyl, or tetrahydronaphthyl each of which is optionally substituted by one to five substituents selected from the group consisting of ($C_1$-$C_7$)alkyl, halo, hydroxyl and ($C_1$-$C_7$) alkoxy; $R_2$ is ($C_1$-$C_7$)alkyl, ($C_6$-$C_{10}$)aryl-($C_1$-$C_7$)alkyl, or (5-9 membered) heteroaryl-($C_1$-$C_7$)alkyl, (5-9 membered) heterocyclyl-($C_1$-$C_7$)alkyl, or mono-($C_1$-$C_7$)alkylamino-($C_1$-$C_7$)alkyl, or di-($C_1$-$C_7$)alkylamino-($C_1$-$C_7$)alkyl; or a pharmaceutically acceptable salt thereof; or an optical isomer thereof; or a mixture of optical isomers.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

The term "aryl" refers to monocyclic or bicyclic aromatic hydrocarbon groups having 6-20 carbon atoms in the ring portion. Preferably, the aryl is a ($C_6$-$C_{10}$)aryl. Non-limiting examples include phenyl, biphenyl, naphthyl or tetrahydronaphthyl, each of which may optionally be substituted by 1-4 substituents, such as optionally substituted alkyl, trifluoromethyl, cycloalkyl, halo, hydroxy, alkoxy, acyl, alkyl-C (O)—O—, aryl-O—, heteroaryl-O—, optionally substituted amino, thiol, alkylthio, arylthio, nitro, cyano, carboxy, alkyl-O—C(O)—, carbamoyl, alkylthiono, sulfonyl, sulfonamido, heterocyclyl and the like.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "carbamoyl" refers to $H_2$NC (O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonamido" refers to alkyl-S (O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S (O)$_2$—N(alkyl)-, heteroaryl-S(O)$_2$—N(alkyl)-, heteroaryl-alkyl-S(O)$_2$—N(alkyl)- and the like.

As used herein, the term "heterocyclyl" or "heterocyclo" refers to an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofurari, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1, 2 or 3 substituents selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxy;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "sulfonyl" refers to R—SO$_2$—, wherein R is hydrogen, alkyl, aryl, heteroaryl, aryl-alkyl, heteroaryl-alkyl, aryl-O—, heteroaryl-O—, alkoxy, aryloxy, cycloalkyl, or heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. As used herein, the term "lower alkoxy" refers to the alkoxy groups having about 1-7 preferably about 1-4 carbons.

As used herein, the term "acyl" refers to a group R—C(O)— of from 1 to 10 carbon atoms of a straight, branched, or cyclic configuration or a combination thereof, attached to the parent structure through carbonyl functionality. Such group may be saturated or unsaturated, and aliphatic or aromatic. Preferably, R in the acyl residue is alkyl, or alkoxy, or aryl, or heteroaryl. Also preferably, one or more carbons in the acyl residue may be replaced by nitrogen, oxygen or sulfur as long as the point of attachment to the parent remains at the carbonyl. Examples include but are not limited to, acetyl, benzoyl, propionyl, isobutyryl, t-butoxycarbonyl, benzyloxycarbonyl and the like. Lower acyl refers to acyl containing one to four carbons.

As used herein, the term "cycloalkyl" refers to optionally substituted saturated or unsaturated monocyclic, bicyclic or tricyclic hydrocarbon groups of 3-12 carbon atoms, preferably 3-7 carbon atoms, each of which may be substituted by one or more substituents, such as alkyl, halo, oxo, hydroxy, alkoxy, alkyl-C(O)—, acylamino, carbamoyl, alkyl-NH—, (alkyl)$_2$N—, thiol, alkylthio, nitro, cyano, carboxy, alkyl-O—C(O)—, sulfonyl, sulfonamido, sulfamoyl, heterocyclyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo [2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

As used herein, the term "aryloxy" refers to both an —O-aryl and an —O-heteroaryl group.

As used herein, the term acylamino refers to the group —NRC(O)R' where each of R and R' is independently hydrogen, alkyl, aryl, heteroaryl, or heterocyclyl, where both R and R' groups are optionally joined to form a heterocyclic group (e.g., morpholino) wherein alkyl, aryl, heteroaryl and heterocyclyl are as defined herein.

As used herein, the term "heteroaryl" refers to a 5-14 membered monocyclic- or bicyclic- or fused polycyclic-ring system, having 1 to 8 heteroatoms selected from N, O or S. Preferably, the heteroaryl is a 5-10 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-, quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b] thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo [1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazol, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halo" or "halogen" refers to fluoro, chloro, bromo, and iodo.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences,* 20th ed., Mack Publishing Company, Easton, Pa., (1985), which is herein incorporated by reference.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces expression or activity of MMP-9, and/or MMP-12 and/or MMP-13.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary,* (W.B. Saunders Co. 27th ed. 1988).

As used herein, the term "inhibition" or "inhibiting" refers to the reduction or suppression of a given condition, symptom, or disease, or a significant decrease in the baseline activity of a biological activity or process. Preferably, the condition is associated with or mediated by MMP-9, and/or MMP-12 and/or MMP-13.

As used herein, the term "treating" or "treatment" of any disease or disorder refers in one embodiment, to ameliorating the disease or disorder (i.e., arresting or reducing the development of the disease or at least one of the clinical symptoms thereof. In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans (E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound, e.g., by fractional crystallization of a salt formed with an optically active acid, Racemic products can also be resolved by chiral chromatography, e.g., high pressure liquid chromatography (HPLC) using a chiral adsorbent.

Finally, compounds of the present invention are either obtained in the free form, as a salt thereof, or as prodrug derivatives thereof.

When a basic group is present in the compounds of the present invention, the compounds can be converted into acid addition salts thereof, in particular, acid addition salts with the imidazolyl moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as ($C_1$-$C_4$)alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as ($C_1$-$C_4$)alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds are inactive or have low activity compared to the corresponding active drug compound, that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-delakylation, oxidative O- and S-delakylation, oxidative deamination, as well as other oxidative reactions.

2. Reductive reactions, such as reduction of carbonyl groups, reduction of alcoholic groups and carbon-carbon double bonds, reduction of nitrogen-containing functions groups, and other reduction reactions.

3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., US20040077595, application Ser. No. 10/656, 838, incorporated herein by reference. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, *The Practice of Medicinal Chemistry*, Ch. 31-32, Ed. Wermuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the pro-drugs, any reference to the compounds of the present invention is to be understood as referring also to the corresponding prodrugs of the compounds of the present invention, as appropriate and expedient.

Furthermore, the compounds of the present invention, including their salts, can also be obtained in the form of their hydrates, or include other solvents used for their crystallization.

The compounds of the present invention have valuable pharmacological properties, they are useful as inhibitors of matrix metalloproteinases such as matrix metalloproteinase 9 (MMP-9), matrix metalloproteinase 12 (MMP-12) and matrix metalloproteinase 13 (MMP-13). MMP-9 also known as gelatinase B acts mainly in the remodeling of extracellular matrix and has been indicated in tumors, autoimmune diseases, chronical obstructive pulmonary disease (COPD), coronary artery diseases and neurodegenerative diseases, etc. See Van den Steen, P et al., *Critical Reviews in Biochemistry and Molecular Biology*, 37(6):375-536 (2002). MMP12, also known as macrophage elastase or metalloelastase, is able to degrade extracellular matrix components such as elastin and is involved in tissue remodeling processes. MMP-12 has been indicated to be a key protein in the pathogenesis of tumor invasiveness, arthritis, atherosclerosis, Alport syndrome, and chronical obstructive pulmonary disease (COPD). MMP-13 also known as collagenase 3, has been indicated (1) in extracellular matrix degradation and cell-matrix interaction associated with metastasis especially as observed in invasive breast cancer lesions and in malignant epithelia growth in skin carcinogenesis; and (2) during primary ossification and skeletal remodelling (M. Stahle-Backdahl et al., (1997) *Lab. Invest.* 76 (5):717-728; N. Johansson et al., (1997) *Dev. Dyn.* 208(3):387-397), in destructive joint diseases such as rheumatoid and osteo-arthritis (D. Wernicke et al., (1996) *J. Rheumatol.* 23:590-595; P. G. Mitchell et al., (1996) *J. Clin. Invest.* 97(3):761-768; O. Lindy et al., (1997) *Arthritis Rheum* 40(8: 1391-1399); and the aseptic loosening of hip replacements (S. Imai et al., (1998) *J. Bone Joint Surg. Br.* 80(4):701-710). MMP13 has also been implicated in chronic adult periodontitis as it has been localized to the epithelium of chronically inflamed mucosa human gingival tissue (V. J. Uitto et al., (1998) *Am. J. Pathol* 152(6):1489-1499) and in remodelling of the collagenous matrix in chronic wounds (M. Vaalamo et al., (1997) *J. Invest. Dermatol.* 109(1): 96-101).

Accordingly, the compounds of the present invention are also useful for treatment of a disorder or a disease mediated by MMP-9, and/or MMP-12, and/or MMP-13. In particular, the compounds of the present invention are useful for treatment of at least one disorder or disease selected from Alport syndrome, asthma, rhinitis, chronic obstructive pulmonary diseases (COPD), arthritis (such as rheumatoid arthritis and osteoarthritis), atherosclerosis and restenosis, cancer invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and Multiple Sclerosis (MS), hematological disorders.

Additionally, the present invention provides:

a compound of the present invention for use as a medicament;

the use of a compound of the present invention for the preparation of a pharmaceutical composition for the delay of progression and/or treatment of a disorder or disease mediated by MMP-9, and/or MMP-12, and/or MMP-13.

the use of a compound of the present invention for the preparation of a pharmaceutical composition for the delay of progression and/or treatment of a disorder or disease mediated by MMP-9, and/or MMP-12, and/or MMP-13.

the use of a compound of the present invention for the preparation of a pharmaceutical composition for the delay of progression and/or treatment of a disorder or disease selected from Alport syndrome, asthma, rhinitis, chronic obstructive pulmonary diseases (COPD), arthritis (such as rheumatoid arthritis and osteoarthritis), atherosclerosis and restenosis, cancer invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and Multiple Sclerosis (MS), hematological disorders.

The compounds of formula (I)-(IV) can be prepared by the procedures described in the following sections.

Generally, the compounds of formula (I) and (III) can be prepared according to Scheme 1, which contains six steps.

Scheme 1

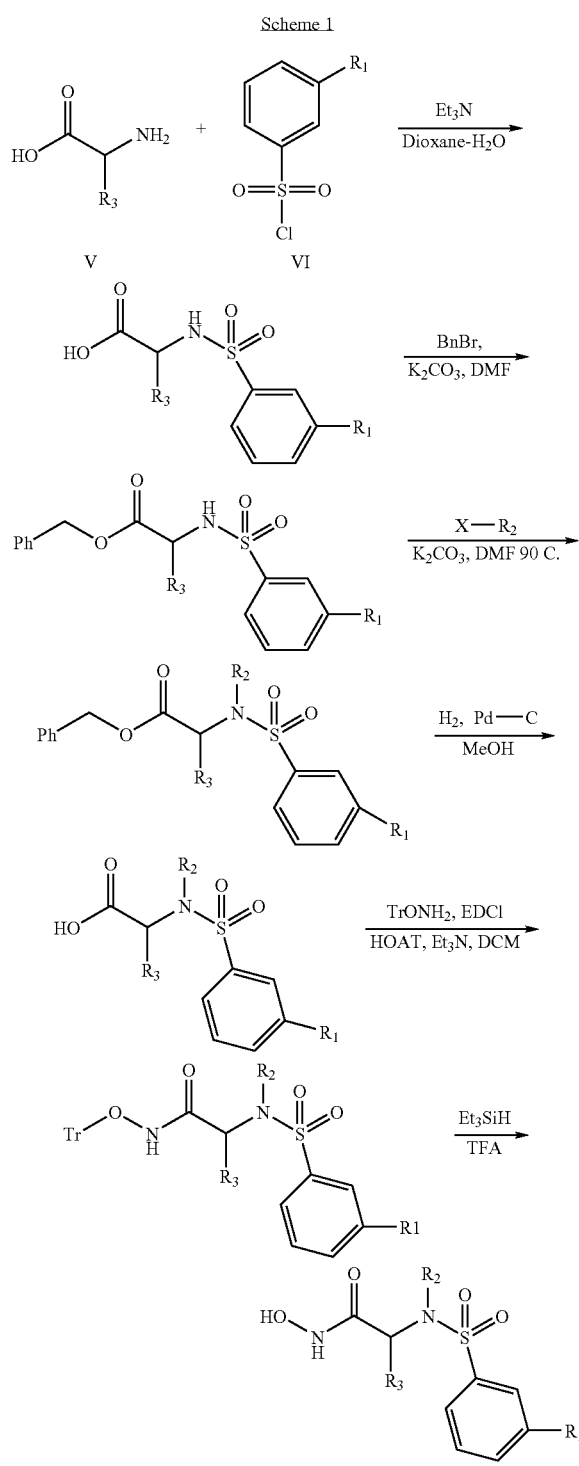

As to the individual steps in the above scheme, step 1 involves the sulfonylation of a amino acid (formula (V)) with a 3-$R_1$-benzene sulfonyl chloride (formula (VI)) to yield an N-aryl sulfonamide substituted amino acid. Step 2 involves protection of the acid functionality as the benzyl ester, which allows for regioselective N alkylation of the sulfonamide nitrogen in step 3. Following the alkylation, the benzyl protecting group is removed via hydrogenolysis and the acid is converted to the hydroxamic acid in a two step procedure using the trityl protected hydroxylamine followed by removal of the trityl protecting group in the last step.

Alternatively, different alkoxy-substituted compounds of formula (I) can be prepared from the benzyl protected intermediate described above (Scheme 1, where X is an acetoxy group), according to Scheme 2, which contains 2 steps. The conversion of the benzyl ester intermediate to the hydroxamic acid is accomplished in the same manner described in Scheme 1

Scheme 2

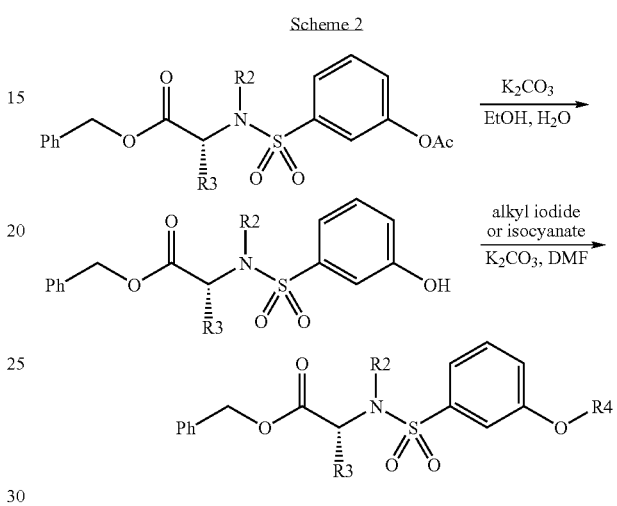

As to the individual steps in Scheme 2, step 1 involves the hydrolysis of the ester to provide the phenolic intermediate, step 2 involves the alkylation of the phenol to give the requisite ether or carbamate, as defined above.

Alternatively, different acylamino-substituted compounds of formula (I) can be prepared from the benzyl protected intermediate described above Scheme 1, where X is a nitro group), according to Scheme 3, which contains 2 steps. The conversion of the benzyl ester intermediate to the hydroxamic acids of Formula (I) is accomplished in the same manner described in Scheme 1

Scheme 3

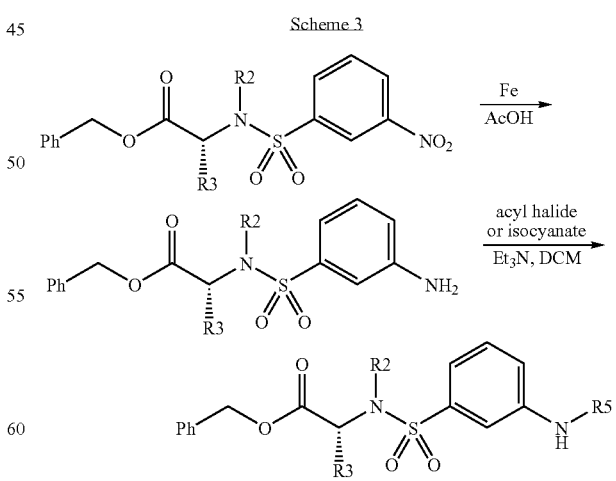

As to the individual steps in Scheme 3, step 1 involves the reduction of the nitro group to the aniline intermediate. Step 2 involves the acylation of the aniline to give the requisite urea or acylamino group as defined above.

Additional compounds of the formula (I) can be prepared in an alternate manner as seen in Scheme 4.

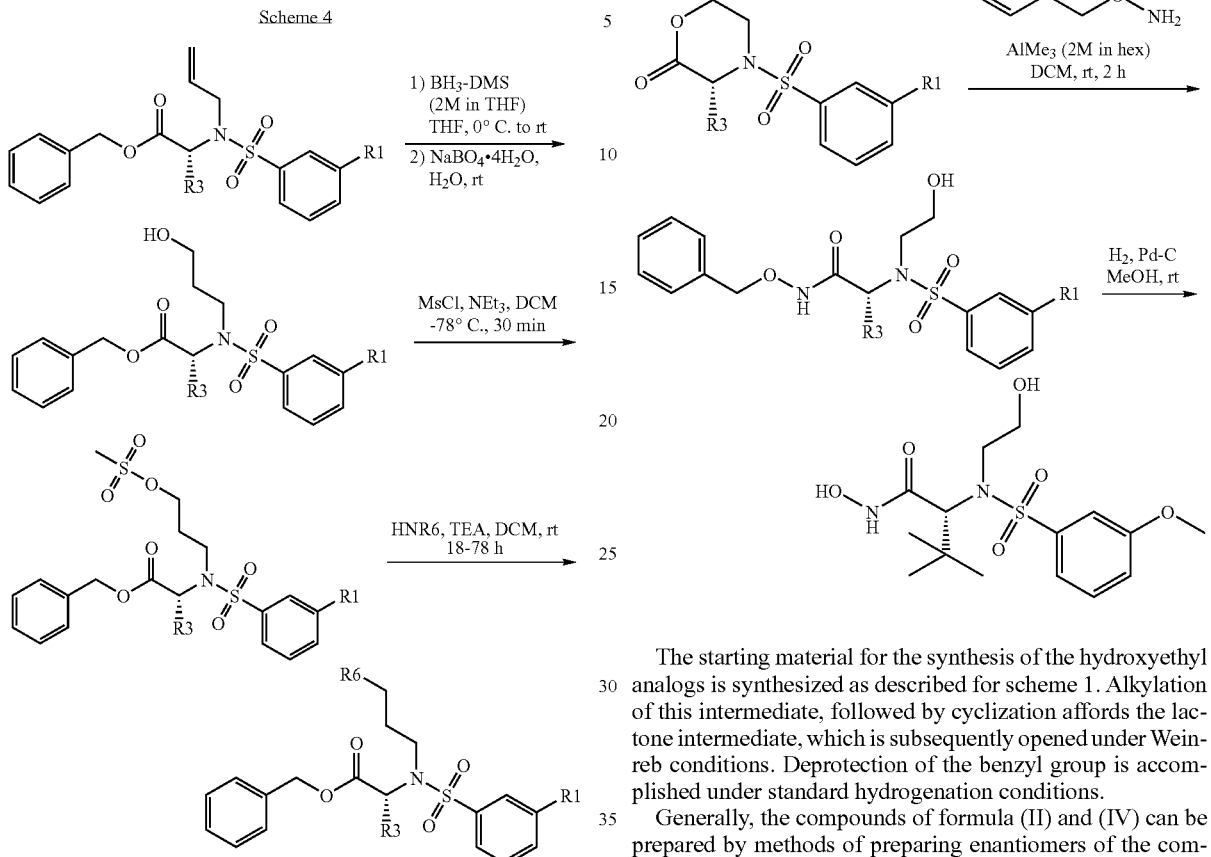

More specifically, the analogs in scheme 4 can be synthesized through a series of chemical transformations starting with the allyl-amine intermediate, which can be prepared in a manner analogous to the alkylation illustrated in scheme 1. Hydroboration of this intermediate, followed by mesylation and subsequent displacement leads to the incorporation of the R6 moiety. In a similar manner to scheme 1, the benzyl ester intermediate is converted to the hydroxamic acids of Formula (I).

Compounds of Formula (I), where R2 is equal to hydroxyethyl, can be synthesized in an alternate fashion to those described above.

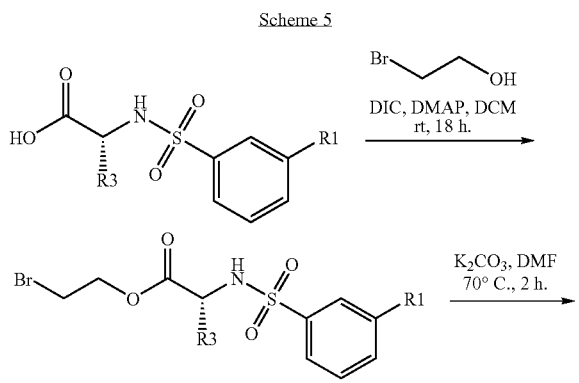

The starting material for the synthesis of the hydroxyethyl analogs is synthesized as described for scheme 1. Alkylation of this intermediate, followed by cyclization affords the lactone intermediate, which is subsequently opened under Weinreb conditions. Deprotection of the benzyl group is accomplished under standard hydrogenation conditions.

Generally, the compounds of formula (II) and (IV) can be prepared by methods of preparing enantiomers of the compounds known to those skilled in the art by resolving racemic mixtures, such as by formation and recrystallization of diastereomeric salts or by chiral chromatography or HPLC separation utilizing chiral stationery phases.

Preferably, the compounds of formula (II) and (IV) can be prepared starting with materials in the form of the intended enantiomer and using the schemes described herein, such that the resulting final compounds are in the form of the intended enantiomer.

In starting compounds and intermediates which are converted to the compounds of the present invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, carboxy, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Preferably, the pharmaceutical compositions are tablets and gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical compositions contain a therapeutically effective amount of a compound of the invention as defined above, either alone or in a combination with another therapeutic agent, e.g., each at an effective therapeutic dose as reported in the art. Such therapeutic agents include 1) $AT_1$ receptor antagonists selected from the group consisting of abitesartan, benzyllosartan, candesartan, elisartan, embusartan, enoltasosartan, eprosartan, fonsartan, forasartan, glycyllosartan, irbesartan, isoteoline, losartan, milfasartan, olmesartan, opomisartan, pratosartan, ripisartan, saprisartan, saralasin, sarmesin, tasosartan, telmisartan, valsartan, zolasartan; Kissei KRH-94, Lusofarmaco LR-B/057, Lusofarmaco LR-B/081, Lusofarmaco LR B/087, Searle SC-52458, Sankyo CS-866, Takeda TAK-536, Uriach UR-7247, A-81282, A-81988, BIBR-363, BIBS39, BIBS-222, BMS-180560, BMS-184698, CGP-38560A, CGP-48369, CGP-49870, CGP-63170, CI-996, CV-11194, DA-2079, DE-3489, DMP-811, DuP-167, DuP-532, GA-0056, E-4177, EMD-66397, EMD-73495, EXP-063, EXP-929, EXP-3174, EXP-6155, EXP-6803, EXP-7711, EXP-9270, FK-739, HN-65021, HR-720, ICI-D6888, ICI-D7155, ICI-D8731, KR1-1177, KT3-671, KW-3433, L-158809, L-158978, L-159282, L-159689, L-159874, L-161177, L-162154, L-162234, L-162441, L-163007, L-163017, LY-235656, LY-285434, LY-301875, LY-302289, LY-315995, ME-3221, PD-123177, PD-123319, PD-150304, RG-13647, RWJ-38970, RWJ-46458, S-8307, S-8308, SL-91.0102, U-96849, U-97018, UP-269-6, UP-275-22, WAY-126227, WK-1492.2K, WK-1360, X-6803, XH-148, XR-510, YM-358, YM-31472, ZD-6888, ZD-7155 and ZD-8731 which are all known per se, or any physiologically compatible salts, solvates, prodrugs or esters thereof; 2) non-selective alpha-adrenoceptor antagonists, e.g. tolazoline or phenoxybenzamine; 3) selective alpha-adrenoceptor antagonists, e.g. doxazosin, prazosin, terazosin or urapidil; beta-adrenoceptor antagonists, e.g. acebutolol, alprenolol, atenolol, betaxolol, bisoprolol, bupranolol, carazolol, carteolol, celiprolol, mepindolol, metipranolol, metoprolol, nadolol, oxprenolol, penbutolol, pindolol, propranolol, sotalol and timolol; 4) mixed antagonists of alpha- and beta-adrenoceptors, e.g. carvedilol or labetolol; ganglion blockers, e.g. reserpine or guanethidine; 5) alpha2-adrenoceptor agonists (including centrally acting alpha2-adrenoceptor agonists), e.g. clonidine, guanfacine, guanabenz methyldopa and moxonidine; 6) rennin inhibitors, e.g. alskiren; 7) ACE inhibitors, e.g. benazepril, captopril, cilazapril, enalapril, fosinopril, imidapril, lisinopril, moexipril, quinapril, perindopril, ramipril, spirapril or trandolapril; 8) mixed or selective endothelin receptor antagonists e.g. atrasentan, bosentan, clazosentan, darusentan, sitaxsentan, tezosentan, BMS-193884 or J-104132; direct vasodilators, e.g. diazoxide, dihydralazine, hydralazine or minoxidil; 9) mixed ACE/NEP dual inhibitors, e.g. omapatrilat; ECE inhibitors, e.g. FR-901533; PD-069185; CGS-26303; CGS-34043; CGS-35066; CGS-30084; CGS-35066; SM-19712; Ro0677447; 10) selective NEP inhibitors; 11) vasopressin antagonists; 12) aldosterone receptor antagonists, e.g. eplerenone; 13) aldosterone inhibitors; 14) angiotensin vaccine; and 15) urotensin II receptor antagonists.

Furthermore, the combinations as described above can be administered to a subject via simultaneous, separate or sequential administration (use). Simultaneous administration (use) can take place in the form of one fixed combination with two or more active ingredients, or by simultaneously administering two or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two compounds are administered such that no overlap of measurable blood levels of both compounds are present in an overlapping manner (at the same time).

Also combinations of two or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

Additionally, the present invention provides:

a pharmaceutical composition or combination of the present invention for use as a medicament;

the use of a pharmaceutical composition or combination of the present invention for the delay of progression and/or treatment of a disorder or disease mediated by MMP-9, and/or MMP-12 and/or MMP-13.

the use of a pharmaceutical composition or combination of the present invention for the delay of progression and/or treatment of a disorder or disease selected from hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

the use of a pharmaceutical composition or combination of the present invention for the delay of progression and/or treatment of a disorder or disease selected from gynecomastia, osteoporosis, prostate cancer, endometriosis, uterine fibroids, dysfunctional uterine bleeding, endometrial hyperplasia, polycystic ovarian disease, infertility, fibrocystic breast disease, breast cancer and fibrocystic mastopathy.

The pharmaceutical composition or combination of the present invention can be in unit dosage of about 1-1000 mg of active ingredients for a subject of about 50-70 kg, preferably about 5-500 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, preferably between about 1-100 mg/kg.

The activities of a compound according to the present invention can be assessed by the following methods well-described in the art. Determination of $IC_{50}$ values in MMP assays Dose-response curves are prepared in DMSO/water solution (90/10, v/v) in 96-well plate format and stored at 4° C. up to 24 hours prior to analysis. In all steps poly-propylene pipette tips are changed avoiding cross-contamination or compound carry over. On the day of the assay, each compound is further diluted (1/33.33; 96-well plate format) in water containing 0.05% CHAPS to 3-times the desired assay concentration. In the assay for each compound, 11 concentrations ranging from 30 to 0.0003 μM are investigated (0.0003, 0.001, 0.003, 0.01, 0.03, 0.1, 0.3, 1, 3, 10, 30 μM). A three-fold concentrated MMP solution is prepared in two-fold concentrated assay buffer 100 mM Tris-HCl buffer, pH 7.5 containing 100 mM NaCl, 10 mM $CaCl_2$, 10 μM $ZnCl_2$, 0.05% Brij-35 and dispensed in 96-well Greiner plates. Similarly a three-fold concentrated substrate solution (15 μM) is prepared in 100 mM Tris-HCl buffer, pH 7.5 containing 100 mM NaCl, 10 mM $CaCl_2$, 10 μM $ZnCl_2$, 0.05% Brij-35 and dispensed in 96-well Greiner plates. Transfer of compounds, substrate and enzyme from 96-well plates to 384-well plates is made using either Cybi™well or Cybi™disk devices.

The assay procedure is the following, in each well, 10 μL water/CHAPS (±test compound) is added, followed by 10 μL human MMP solution (final assay concentration 0.5 nM). After 1 hour of incubation at room temperature the assay is started by addition of 10 μL substrate solution (final concentration 5 μM).

The reaction is allowed to proceed for 1 hours at ambient temperature (~20-22° C.). At the end of the incubation the fluorescence is measured as described above.

The apparent inhibition constant, $IC_{50}$, is determined from the plot of percentage of inhibition vs. inhibitor concentration using non-linear regression analysis software (XLfit, Vers. 3.0.5; ID Business Solution Ltd., Guildford, Surrey, UK).

In vivo models which are useful for the study of MMP inhibitors have been reported in the literature. Some of these can be found in the following references: "Role of MMP-9 and MMP-12 in Atherosclerosis" Luttun et al in *Circulation*. 2004; 109:1408-1; "Macrophage Metalloelastase as a Major Factor for Glomerular Injury in Anti-Glomerular Basement Membrane Nephritis" Kaneko et. al *The Journal of Immunology*, 2003, 170: 3377-3385; "MMP-12 has a role in abdominal aortic aneurysms in mice" Longo et al *Surgery* 2005; 137:457-62; "Expression and Localization of Macrophage Elastase (Matrix Metalloproteinase-12) in Abdominal Aortic Aneurysms" Curci et. al *J. Clin. Invest.* 1998. 102:1900-D1910.

| # | Compound | MMP02 IC50 (μM) | MMP13 IC50 (μM) | MMP12 IC50 (μM) | MMP09 IC50 (μM) |
|---|---|---|---|---|---|
| 2-4 | 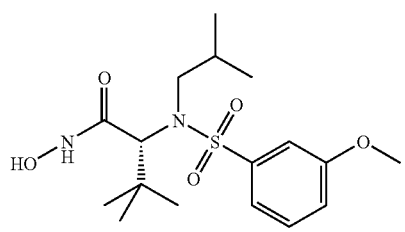 | 1.7 | 0.095 | 0.0175 | 0.725 |
| 2-6 | | 11.1 | 0.25 | 0.0175 | 1.5 |

| # | Compound | MMP02 IC50 (μM) | MMP13 IC50 (μM) | MMP12 IC50 (μM) | MMP09 IC50 (μM) |
|---|---|---|---|---|---|
| 2-7 | | 13.95 | 0.5 | 0.225 | 7.825 |
| 2-13 | | 10.25 | 1.15 | 0.035 | 17.35 |
| 2-17 | | 28.256 | 2.4382 | 0.226275 | 12.49255 |
| 2-23 | | 12.5 | 0.8 | 0.145 | 3.5 |
| 2-26 | | 8.75 | 0.85 | 0.055 | 3.7 |
| 2-27 | | 40.25 | 4.95 | 0.3 | 22.7 |

-continued

| # | Compound | MMP02 IC50 (μM) | MMP13 IC50 (μM) | MMP12 IC50 (μM) | MMP09 IC50 (μM) |
|---|---|---|---|---|---|
| 2-28 | | 3.15 | 1.55 | 0.05 | 3.1 |
| 2-34 | | 3.7 | 1.2 | 0.065 | 6.9 |
| 2-38 | | >30 | 25.45 | 0.65 | >30 |
| 2-39 | | >30 | 6.55 | 0.4 | >30 |
| 4-4 | | 1.35 | 0.05 | 0.0015 | 0.9 |

US 8,232,427 B2

-continued

| # | Compound | MMP02 IC50 (μM) | MMP13 IC50 (μM) | MMP12 IC50 (μM) | MMP09 IC50 (μM) |
|---|---|---|---|---|---|
| 5 | | 7.7 | 0.07 | 0.0055 | 0.4 |
| 6 | | 3 | 0.03 | 0.002 | 0.3 |

Abbreviations:

| | |
|---|---|
| DMSO: | Dimethyl sulfoxide |
| CHAPS: | 3-[(3-Cholamidopropyl)dimethylammonio]-1-propanesulfonate PC/4-50124A/USN |
| DMF: | Dimethyl Formamide |
| Hex-EtOAc: | Hexanes/Ethyl Acetate |
| DCM: | Dichloromethane |
| HOAT: | 1-Hydroxy-7-azabenzotriazole |
| EDCI: | N-(3-Dimethylaminopropyl)-N'-ethylcarbodiimide |
| HCl: | Hydrochloric acid |
| MgSO$_4$: | Magnesium sulfate |
| K$_2$CO$_3$: | Potatssium carbonate |
| MeOH: | Methanol |
| DIAD: | Diisopropyl azodicarboxylate |
| THF: | Tetrahydrofuran |
| DMS: | Dimethylsulfide |
| DIPEA: | Diisopropylethylamine |
| DIC: | N,N'-Diisopropylcarbodiimide |
| DMAP: | 4-Di(methylamino)pyridine |
| 9-BBN: | 9-Borabicyclo[3.3.1]nonane |
| Pd(PPh$_3$)$_4$: | Tetrakis(triphenylphosphine)palladium(0) |
| rt: | Room temperature |

EXAMPLES

The present invention will now be illustrated by reference to the following examples which set forth particularly advantageous embodiments. However, it should be noted that these embodiments are illustrative and are not to be construed as restricting the invention in any way. The compounds in the following examples have been found to have IC50 values for MMP-9, MMP-12 and MMP-13 in the range of about 0.1 nM to about 10 μM.

Example 1

N-isoamyl-N-(3 Methoxyphenylsulfonyl)D-tert-leucine hydroxamic acid

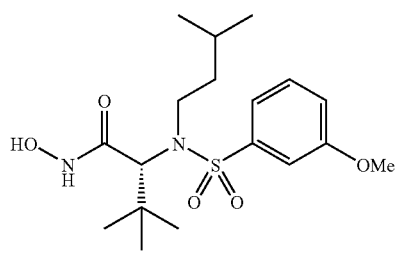

This compound is prepared in 6 steps according to the sequence illustrated above in Scheme 1 as follows:

Step 1: N-(3 Methoxyphenylsulfonyl)D-tert-leucine

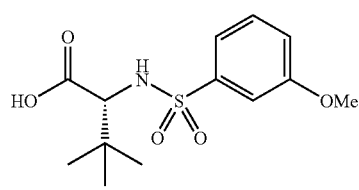

D-tert-leucine (3 g, 22.9 mmol), 3-methoxy benzenesulfonyl chloride (4.68 g, 22.6 mmol) and triethylamine (6.4 ml, 45.7 mmol) are stirred in dioxane-water (1:1, 60 ml) at ambient temperature for 20 minutes. The reaction mixture is concentrated in vacuo and the residue is re-dissolved in Ethyl Acetate and washed with 1 N HCl. The organics are separated and washed with brine. The organic layer is dried over MgSO$_4$ and concentrated to afford the title compound as a white solid (6.36 g, 92% yield). $^1$H-NMR (CDCl$_3$, 400 MHz): δ 7.49 (d, 1H, J=8), 7.39 (s, 1H), 7.32 (t, 1H, J=8.11), 7.00 (m, 1H), 5.67 (d, 1H, J=12), 3.86 (s, 3H), 3.42 (d, 2H, J=8), 1.01 (s, 9H). Mass spectrum (302.0; M+1, 300.0; M−1).

Step 2: N-(3 Methoxyphenylsulfonyl)D-tert-leucine benzyl ester

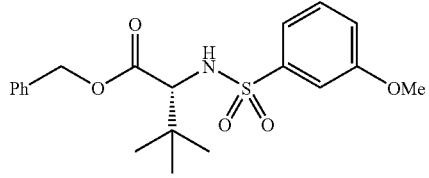

N-(3 Methoxyphenylsulfonyl)D-tert-leucine (3.03 g, 10.1 mmol) is dissolved in DMF (30 ml). Potassium Carbonate (2.81 g, 20.1 mmol) is added followed by Benzyl Bromide (1.21 ml, 9.95 mmol) and the reaction is stirred at ambient temperature for 18 hours. The reaction mixture is partitioned between Ethyl Acetate and 1 N HCl. The organics are separated and washed with brine, dried over MgSO$_4$ and concentrated. The residue is purified by column chromatography eluting with a gradient of 5-60% (Hex-EtOAc) to give the title compound (3.08 g, 78% yield). Mass spectrum (392.2; M+1, 390.2; M−1).

Step 3: N-isoamyl-N-(3 Methoxyphenylsulfonyl)D-tert-leucine benzyl ester

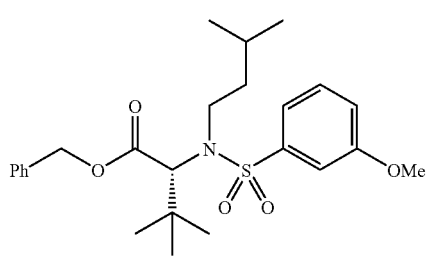

To a solution of N-(3 Methoxyphenylsulfonyl)D-tert-leucine benzyl ester (1.31 g, 3.35 mmol) in DMF (10 ml) is added K$_2$CO$_3$ (1.87 g, 13.4 mmol) followed by 1-iodo-3-methyl butane (1.33 g, 6.69 mmol) and the reaction mixture is heated to 70° C. overnight. The reaction is cooled to room temperature and then poured over 1 N HCl and extracted with Ethyl Acetate. The organics are washed with brine, dried over MgSO$_4$ and concentrated. The crude product is purified by column chromatography eluting with a gradient of 5-40% (Hex-EtOAc) affording the title compound as a colorless oil (1.0 g, 65% yield). Mass spectrum (462.3; M+1).

Step 4: N-isoamyl-N-(3 Methoxyphenylsulfonyl)D-tert-leucine

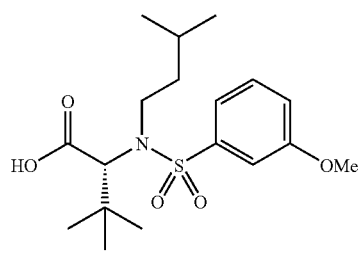

To a solution of N-isoamyl-N-(3 Methoxyphenylsulfonyl) D-tert-leucine benzyl ester (2.0 g, 4.33 mmol) in MeOH (12 ml) is added 10% palladium on carbon (200 mg) and the reaction is stirred under ambient pressure of hydrogen for 4 hours. The reaction is filtered through celite and concentrated affording the title compound (1.6 g, 99%).

H-NMR (CDCl$_3$, 400 MHz): δ 7.35 (d, 1H, J=8), 7.31-7.26 (m, 2H), 6.99 (m, 1H), 4.26 (s, 1H), 3.77 (s, 3H), 3.39-3.32 (m, 1H), 3.21-3.13 (m, 1H), 1.88-1.85 (m, 1H), 1.54-1.53 (m, 2H) 1.03 (s, 9H), 0.88-0.78 (m, 6H). Mass spectrum (372.2; M+1, 370.2; M−1).

Step 5: N-isoamyl-N-(3 Methoxyphenylsulfonyl)D-tert-leucine O-trityl hydroxamic acid

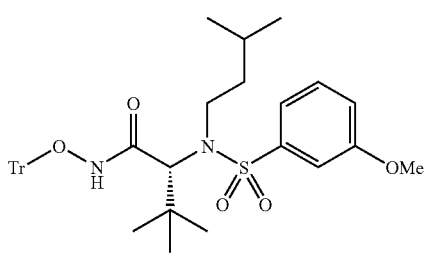

To a solution of N-isoamyl-N-(3 Methoxyphenylsulfonyl) D-tert-leucine (2.0 g, 5.38 mmol) in DCM (50 ml) is added HOAT (1.45 g, 10.8 mmol), EDCI (2.12 g, 10.8 mmol), O-trityl hydroxylamine (2.96 g, 10.8 mmol) and triethylamine (1.51 ml, 10.8 mmol) and the reaction mixture is stirred at ambient temperature for 18 hours. The reaction is quenched with 1 N HCl and extracted with dichloromethane. The combined organic layers are washed with brine and concentrated. The crude product is purified by column chromatography eluting with a gradient of 5-40% (Hex-EtOAc) affording the title compound (2.8 g, 83%). H-NMR (CDCl$_3$, 400 MHz): δ 7.46-7.44 (m, 9H), 7.37-7.18 (m, 10H), 7.03 (m, 1H), 4.95 (s, 1H), 3.87 (s, 3H), 3.57-3.53 (m, 1H), 3.44-3.38

(m, 2H), 1.93-1.88 (m, 1H), 1.55-1.45 (m, 2H), 0.95-0.87 (m, 6H), 0.73 (s, 9H). Mass spectrum (627.4; M−1).

Step 6: N-isoamyl-N-(3 Methoxyphenylsulfonyl)D-tert-leucine hydroxamic acid

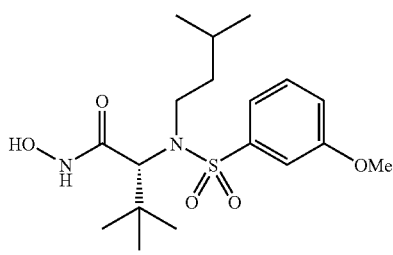

To a solution of N-isoamyl-N-(3 Methoxyphenylsulfonyl) D-tert-leucine O-trityl hydroxamic acid (2.8 g, 4.45 mmol) in DCM (25 ml) is added trifluoroacetic acid (2.76 ml, 35.6 mmol) followed by triethyl silane (1.45 g, 8.9 mmol) and the reaction is allowed to stir at ambient temperature for 10 minutes. The reaction is diluted with DCM, washed with water and brine, dried over $MgSO_4$ and concentrated by half. The precipitated product is collected by filtration, washed with hexanes and dried in vacuo affording the title compound as a white solid (0.82 g, 48%). H-NMR (MeOD, 400 MHz): δ 7.44 (m, 2H), 7.38 (s, 1H), 7.17 (m, 1H), 4.03 (m, 2H), 3.87 (s, 3H), 3.18 (m, 1H), 1.85 (m, 1H), 1.52-1.41 (m, 2H), 1.12 (s, 9H), 0.95 (s, 6H). MP 115.5-116.5. Mass spectrum (387.1; M+1, 385.2; M−1). CHN CalcCHN 55.94, 7.82, 7.25 Found CHN 55.84, 8.01, 7.10.

Example 2

The following compounds are prepared analogously to Example 1 starting from the requisite amino acid ester derivative.

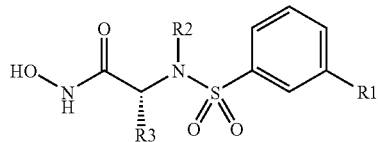

| Example | R1 | R2 | R3 | e/z |
|---|---|---|---|---|
| 2-1 | MeO | H | t-butyl | M + H: 317.1 |
| 2-2 | Me | Isopentyl | t-butyl | M − H: 369.2 |
| 2-3 | MeO | n-Propyl | t-butyl | M − H: 357.1 |
| 2-4 | Cl | Isopentyl | t-butyl | M − H: 389.2 |
| 2-5 | F | Isopentyl | t-butyl | M − H: 373.3 |
| 2-6 | MeO | Isobutyl | t-butyl | M − H: 371.5 |
| 2-7 | Et | Isopentyl | t-butyl | M − H: 383.5 |
| 2-8 | CF$_3$O | Isopentyl | t-butyl | M − H: 439.4 |
| 2-9 | Br | Isopentyl | t-butyl | M − H: 433.2, 435.2 |
| 2-10 | MeO | Methyl | t-butyl | M + H: 331.0 |
| 2-11 | MeO | Ethyl | t-butyl | M − H: 343 |
| 2-12 | CH$_3$C(O)— | Isopentyl | t-butyl | M + H: 399.2 |
| 2-13 | CH3(CO)NH— | Isopentyl | t-butyl | M + H: 414.3 |
| 2-14 | Me | Isopentyl | Isopropyl | M + H: 357.1 |
| 2-15 | Cyano | Isopentyl | Isopropyl | M − H: 366.1 |
| 2-16 | MeO | Isopentyl | Isopropyl | M + H: 373.3 |
| 2-17 | EtO | Isopentyl | Isopropyl | M + H: 387.4 |
| 2-18 | i-BuO | isopentyl | isopropyl | M + H: 415.4 |
| 2-19 | Et(CO)NH— | isopentyl | t-butyl | M + H: 428.3 |
| 2-20 | iPr-(CO)NH— | Isopentyl | t-butyl | M + H: 442.3 |
| 2-21 | EtNH(CO)NH— | isopentyl | t-butyl | M + H: 443.3 |
| 2-22 | EtO—(CO)—NH— | isopentyl | t-butyl | M + H: 444.3 |
| 2-23 | MeO | Benzyl | t-butyl | M + H: 407.2 |
| 2-24 | Et | n-Propyl | t-butyl | M + H: 357.2 |
| 2-25 | Et | Isobutyl | t-butyl | M + H: 371.2 |
| 2-26 | MeO | MeO(CO)CH2— | t-butyl | M + H: 390.1 |
| 2-27 | MeO | Me2N(CO)CH2— | t-butyl | M + H: 402.3 |
| 2-28 | NH2 | Isoamyl | t-butyl | M + H: 372.3 |
| 2-29 | Et(CO)NH— | Isoamyl | t-butyl | M + H: 428.3 |
| 2-30 | H(CO)NH— | Isoamyl | t-butyl | M + H: 400.3 |
| 2-31 | nPr(CO)NH— | Isoamyl | t-butyl | M + H: 442.5 |
| 2-32 | MeNH(CO)NH— | Isoamyl | t-butyl | M + H: 429.4 |
| 2-33 | nPrNH(CO)NH— | Isoamyl | t-butyl | M + H: 457.4 |
| 2-34 | iPrNH(CO)NH— | Isoamyl | t-butyl | M + H: 457.4 |
| 2-35 | BnNH(CO)NH— | Isoamyl | t-butyl | M + H: 505.5 |
| 2-36 | EtNH(CO)O— | Isoamyl | t-butyl | M + H: 444.2 |
| 2-37 | EtNH(CO)— | n-Propyl | t-butyl | M + H: 400.5 |
| 2-38 | MeNH(CO)— | n-Propyl | t-butyl | M + H: 386.4 |
| 2-39 | MeO(CO)— | n-Propyl | t-butyl | M − H: 385.3 |
| 2-40 | HO(CO)— | n-Propyl | t-butyl | M − H: 371.3 |
| 2-41 | EtNH(CO)NH— | n-Propyl | t-butyl | M + H: 415.5 |
| 2-42 | MeO | 3-picolyl | Isopropyl | M + H: 379.1 |
| 2-43 | MeO | 3-picolyl | t-butyl | M + H: 408.1 |

Alternate to Step 3 (for picolyl analogs 2-42 and 2-43):

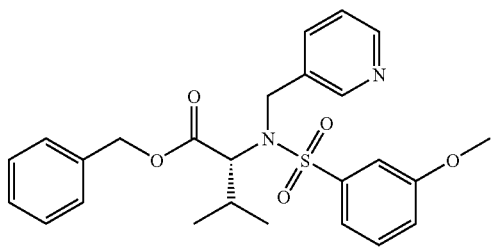

To a solution of N-(3 Methoxyphenylsulfonyl)D-tert-leucine benzyl ester (500 mg, 1.33 mmol) in THF (7 mL) cooled to 0° C. is added triphenylphospine (427.5 mg, 1.46 mmol), 3-pyridylcarbinol (0.142 mL, 1.46 mmol), and DIAD (0.287 mL, 1.46 mmol). The reaction is warmed to room temperature and stirred overnight. The reaction is diluted with ethyl acetate, washed with brine, and the organic layer is dried with sodium sulfate and concentrated. The crude product is purified using column chromatography eluting with a gradient of 25-100% ethyl acetate in heptane containing 1% triethylamine to afford the product as a clear oil (623 mg, 100%). Mass spectrum (469.1; M+1).

Example 3

$N^2$-[3-(Dimethylamino)propyl]-N-hydroxy-$N^2$-[(3-methoxyphenyl)sulfonyl]-3-methyl-D-valinamide

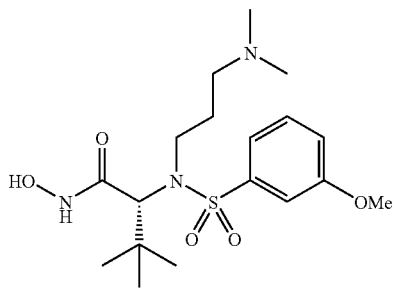

This compound is prepared according to the sequence illustrated above in Scheme 4 as follows:

Step 1: Benzyl N-(3-hydroxypropyl)-N-[(3-methoxyphenyl)sulfonyl]-3-methyl-D-valinate

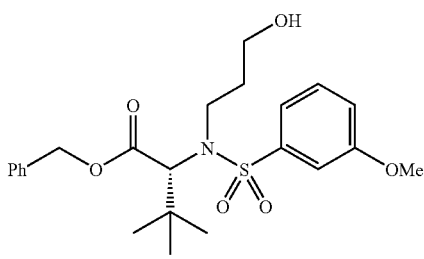

To a solution of benzyl N-allyl-N-[(3-methoxyphenyl)sulfonyl]-3-methyl-D-valinate (12.7 g, 29.3 mmol) in THF (90 mL) cooled to 0° C., borane-DMS complex (5M in diethyl ether, 12 mL, 60.0 mmol) is added dropwise. The reaction mixture is slowly warmed up to rt and is allowed to stir at rt for 24 h. To the reaction mixture, sodium perborate tetrahydrate (27.1 g, 176 mmol) and de-ionized water (90 mL) are added in portions. The reaction mixture is stirred for additional 3 h. The reaction mixture is filtered to remove the white precipitates, then the aqueous layer is extracted with EtOAc. The organic extracts are combined, washed with brine, dried over sodium sulfate, and concentrated in vacuo to obtain a highly viscous yellow oil. The crude product is purified by column chromatography eluting with a gradient of 25-65% EtOAc/heptane to obtain the desired alcohol as a colorless oil (9.08 g). Mass spectrum (450.46; M+1).

Step 2: Benzyl N-[(3-methoxyphenyl)sulfonyl]-3-methyl-N-{3-[(methylsulfonyl)oxy]propyl}-D-valinate

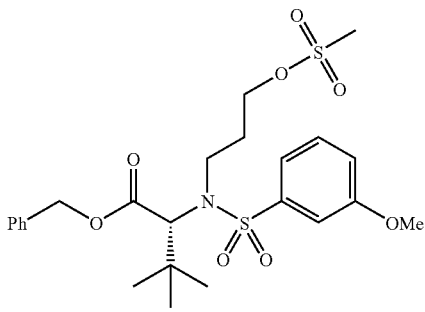

To a solution of benzyl N-(3-hydroxypropyl)-N-[(3-methoxyphenyl)sulfonyl]-3-methyl-D-valinate (9.08 g, 20.2 mmol) and triethylamine (4.2 mL, 30.3 mmol) in DCM (15 mL) cooled to −78° C., methanesulfonyl chloride (1.9 mL, 24.2 mmol) is added dropwise, and the reaction mixture is allowed to stir at −78° C. for 20 min. The reaction mixture is warmed up to rt, washed with de-ionized water, then concentrated in vacuo. The crude product is purified by column chromatography eluting with a gradient of 25-100% EtOAc/heptane to obtain the desired mesylate (9.45 g, 89% yield). Mass spectrum (528.46; M+1).

Step 3: Benzyl N-[3-(dimethylamino)propyl]-N-[(3-methoxyphenyl)sulfonyl]-3-methyl-D-valinate

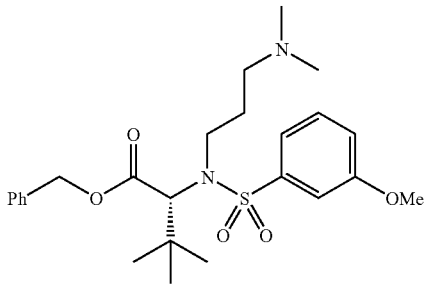

To a solution of benzyl N-[(3-methoxyphenyl)sulfonyl]-3-methyl-N-{3-[(methylsulfonyl)oxy]propyl}-D-valinate (2.00 g, 3.79 mmol) in DCM (15 mL), dimethylamine in THF (2M, 9.5 mmol, 19.0 mmol) and DIPEA (1.99 mL, 11.4 mmol) are added, and the reaction mixture is allowed to stir at rt for 18 h. Additional 3.0 mL of dimethylamine in THF (2M) is added to the reaction mixture and is allowed to stir for additional 3 d. The reaction was approximately 50% complete. The reaction mixture is concentrated in vacuo and is purified by silica gel chromatography eluting with a gradient of 5-100% EtOAc/heptane to obtain the desired intermediate (500 mg, 28% yield). Mass spectrum (477.5; M+1).

Step 4: $N^2$-[3-(Dimethylamino)propyl]-N-hydroxy-$N^2$-[(3-methoxyphenyl)sulfonyl]-3-methyl-D-valinamide

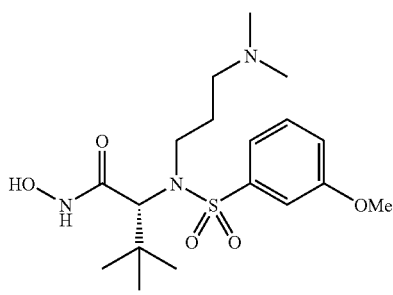

To a de-gassed solution of benzyl N-[3-(dimethylamino)propyl]-N-[(3-methoxyphenyl)sulfonyl]-3-methyl-D-valinate (500 mg, 0.634 mmol) in methanol (10 mL), catalytic palladium on carbon (10% on activated carbon, 7 mg, 0.063 mmol) is added and the reaction mixture is stirred vigorously under hydrogen for 78 h. The reaction mixture is diluted with anhydrous DMF (5 mL), concentrated in vacuo to remove methanol. To the DMF solution of the acid intermediate, O-(tetrahydro-2H-pyranyl)hydroxylamine (149 mg, 1.27 mmol), EDC.HCl (249 mg, 1.27 mmol), and HOAt (173 mg, 1.27 mmol) are added at rt. The reaction was allowed to stir at rt for 18 h and was complete by LC/MS. To the reaction mixture, sodium bicarbonate decahydrate (779 mg, 2.64 mmol) is added and is stirred vigorously for 30 min. The decahydrate crystals are filtered, and the filtrate is concentrated in vacuo, and purified by silica gel chromatography eluting with 15-100% EtOAc/heptanes to obtain 250 mg of the THP-protected hydroxamide intermediate. (81% yield over 2 steps). To the solution of the intermediate in methanol (1 mL), concentrated hydrochloric acid solution (37% in water, 840 mL, 0.70 mmol) is added dropwise. The reaction mixture is stirred for 15 min, resulting in the precipitation of slightly pink white solid. The precipitate is washed with methanol and ether, then dried in vacuo to give the desired product as a white solid (227 mg, 100% yield). $^1$H NMR (400 MHz, $d_6$-DMSO) δ ppm 10.82 (s, 1H), 9.86 (brs, 1H), 8.91 (s, 1H), 7.52-7.90 (m, 2H), 7.35 (m, 1H), 7.24 (m, 2H), 3.98 (m, 1H), 3.97 (s, 1H), 3.85 (s, 3H), 3.07 (ddd, J=12, 4, 4 Hz, 1H), 2.97 (m, 2H), 2.73 (brs, 6H), 2.13 (m, 1H), 1.94 (m, 1H), 1.01 (s, 9H). Mass spectrum (402.20; M+1).

Example 4

The following compounds are prepared analogously to Example 3 starting from the requisite amino acid ester derivative.

| Example | R1 | R6 | e/z |
|---|---|---|---|
| 4-1 | MeO | piperidine | M + H: 442.2 |
| 4-2 | MeO | morpholine | M + H: 444.2 |
| 4-3 | MeO | N-methylpiperazine | M + H: 457.3 |
| 4-4 | EtNH(CO)NH— | piperidine | M + H: 498.2 |
| 4-5 | EtNH(CO)NH— | morpholine | M + H: 500.5 |

Example 5

The following compound is prepared analogously to example 4, however incorporation of the pyridine moiety is accomplished through a Suzuki coupling.

(R)-2-[(3-Methoxy-benzenesulfonyl)-(3-pyridin-3-yl-propyl)-amino]-3,3-dimethyl-butyric acid benzyl ester

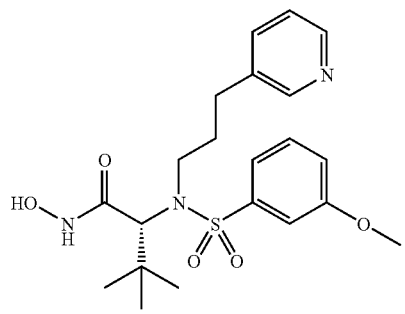

To a solution of benzyl N-allyl-N-[(3-methoxyphenyl)sulfonyl]-3-methyl-D-valinate (222.6 mg, 0.5 mmol) in THF (1 mL) cooled to 0° C. is slowly added a 0.5M solution of 9-BBN (3.0 mL, 1.50 mmol) in THF. The mixture is slowly warmed to room temperature and stirred for two days. This solution is then added to a separate flask containing 3-bromopyridine, Pd(PPh$_3$)$_4$ (57.7 mg, 0.05 mmol), and potassium carbonate (276.2 mg, 2 mmol) in DMF (3.3 mL). The resulting mixture is heated to 70° C. and stirred overnight. The reaction is diluted with ethyl acetate and poured into water. The aqueous layer is extracted three times with ethyl acetate, and the combined organic extracts are washed with brine, dried with sodium sulfate, and concentrated. The crude residue is purified by column chromatography eluting with a gradient of 15-100% ethyl acetate in heptane to yield the desired product as a clear oil (130 mg, 59%). 1H NMR (CDCl$_3$, 400 MHz); δ 8.48 (d, 1H, J=4), 8.43 (s, 1H), 7.58 (d, 1H, J=8), 7.35-7.33 (m, 3H), 7.29-7.27 (m, 1.5H), 7.25-7.23 (m, 1.5H), 7.19-7.18 (m, 2H), 7.05-7.03 (d, 1H, J=8), 4.87 (d, 1H, J=12), 4.69-4.66 (d, 1H, J=12H), 4.36 (s, 1H), 3.74 (s, 3H), 3.57 (m, 1H), 3.18 (m, 1H), 2.58 (t, 2H, J=4), 2.41 (m, 1H), 2.05 (m, 1H), 1.05 (s, 9H). Mass spectrum (511.5; M+1).

Example 6

N-hydroxy-N$^2$-(3-hydroxypropyl)-N$^2$-[(3-methoxyphenyl)sulfonyl]-3-methyl-D-valinamide

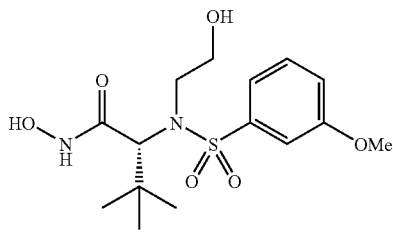

Steps 1-2: (3R)-3-tert-butyl-4-[(3-methoxyphenyl) sulfonyl]morpholin-2-one

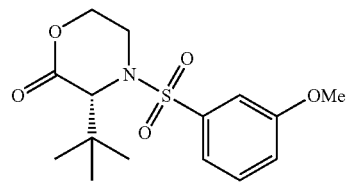

To a solution of N-(3 Methoxyphenylsulfonyl)D-tert-leucine (1.50 g, 4.98 mmol) in DCM cooled to 0° C. with an ice-brine bath, DIC (1.54 mL, 9.95 mmol) and DMAP (122 mg, 1.00 mmol) are added. The reaction mixture is stirred for 5 min at 0° C., then, 2-bromoethanol (562 µL, 7.96 mmol) is added dropwise. The reaction mixture is allowed to slowly warm up to rt, then, stirred for 18 h. The white precipitate is filtered, then, the reaction mixture is concentrated in vacuo. The crude intermediate was purified by silica gel chromatography eluting with 5-80% EtOAc/heptane to obtain the desired intermediate (1.59 g, 78% yield). To a solution of the (R)-2-(3-Methoxy-benzenesulfonylamino)-3,3-dimethyl-butyric acid 2-bromo-ethyl ester intermediate (1.59 g, 3.90 mmol) in DMF (19 mL), potassium carbonate (2.15 g, 15.6 mmol) is added, and the reaction mixture is heated at 70° C. for 2 h. The reaction mixture is bi-partitioned between diethyl ether and water. The organic layer is separated, the aqueous layer is back-extracted with diethyl ether. The organic extracts are combined, washed with brine, dried over sodium sulfate, and concentrated in vacuo to obtain the crude product as a viscous yellow oil. The crude intermediate is purified by silica gel chromatography eluting with 5-100% EtOAc/heptane to obtain the desired cyclic lactone product (500 mg, 39% yield) and 310 mg of the ring-opened by-product (15% yield). Mass spectrum (328.2; M+1).

Steps 3-4: N-hydroxy-N$^2$-(3-hydroxypropyl)-N$^2$-[(3-methoxyphenyl)sulfonyl]-3-methyl-D-valinamide

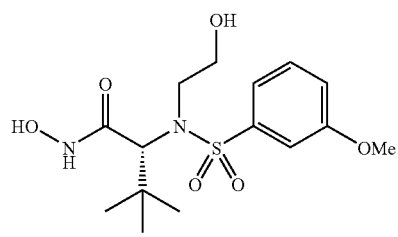

To a solution of (3S)-3-tert-butyl-4-[(3-methoxyphenyl) sulfonyl]morpholin-2-one (260 mg, 0.79 mmol) in anhydrous DCM (2 mL), O-benzylhydroxylamine (358 µL, 3.07 mmol) is added and the reaction mixture is stirred at rt for 30 min, then trimethylaluminum (2M in hexanes, 1.5 mL, 3.00 mmol) is added dropwise under nitrogen. The resulting reaction mixture is stirred at rt for 1 h. The reaction is quenched with pH7 phosphate buffer. The reaction mixture is extracted with DCM, then the combined organic extracts are washed with brine, dried over sodium sulfate, concentrated in vacuo. The crude reaction mixture is purified by silica gel chromatography eluting with a gradient of 5-100% EtOAc/heptane to obtain the desired O-benxylhydroxamide intermediate (541 mg, 100% yield). To a degassed solution of the O-benzylhydroxamide intermediate (100 mg, 0.22 mmol) in methanol (2 mL), catalytic palladium on activated carbon (2 mg, 0.022 mmol) is added, and the reaction mixture is stirred under hydrogen for 1 h. The reaction mixture is filtered and concentrated in vacuo. The resulting crude product is purified by a reverse-phase Gilson HPLC to obtain the desired product (45 mg, 56% yield). $^1$H NMR (400 MHz, d$_4$-methanol) δ ppm 7.50-7.41 (m, 2H), 7.36 (m, 1H), 7.18 (m, 1H), 4.16 (ddd, J=16, 12, 4 Hz, 1H), 3.98 (s, 1H), 3.95 (ddd, J=20, 16, 4 Hz, 1H), 3.87 (s, 3H), 3.72 (ddd, J=20, 16, 4 Hz, 1H), 3.24 (ddd, J=16, 12, 4 Hz, 1H), 1.08 (s, 9H). Mass spectrum (361.1; M+1).

Example 7

The following compound is prepared analogously to Example 6 starting from the requisite amino acid ester derivative.

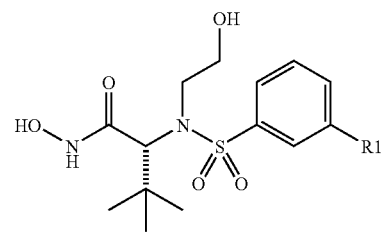

| Example | R1 | e/z |
|---|---|---|
| 7-1 | EtNH(CO)NH— | M + H: 417.2 |

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

We claim:
1. A compound of formula (I)

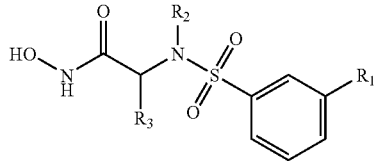

(I)

wherein
R$_1$ is cyano, (C$_1$-C$_7$)alkyl, R$_4$—O—, (C$_1$-C$_7$)alkyl-NHC(O)—, R$_6$C(O)—, or R$_9$—C(O)—O—, wherein
R$_4$, R$_6$, and R$_9$ are independently hydrogen, (C$_1$-C$_7$)alkyl, mono- or di-(C$_1$-C$_7$)alkylamino or aryl each of which is optionally substituted by one to five substituents selected from the group consisting of (C$_1$-C$_7$)alkyl, halo, hydroxyl, (C$_1$-C$_7$)alkoxy and aryl;
R$_2$ is (C$_1$-C$_7$)alkyl which is optionally substituted by one to three substituents selected from the group consisting of (C$_1$-C$_7$)alkyl, hydroxy, aryl, heterocyclyl, heteroaryl, (C$_1$-C$_7$)alkyl-O—C(O)—, di-(C$_1$-C$_7$)alkylamino-C(O)—, wherein each of aryl, heterocyclyl, and heteroaryl is further optionally substituted by (C$_1$-C$_7$)alkyl; or
R$_3$ is (C$_1$-C$_7$)alkyl, or cycloalkyl;
a pharmaceutically acceptable salt thereof; or an optical isomer thereof; or a mixture of optical isomers.

2. The compound of claim 1, wherein
R$_1$ is (C$_1$-C$_7$)alkyl, or R$_4$—O—, wherein R$_4$ is (C$_1$-C$_7$)alkyl optionally substituted by one to three halo,
R$_2$ is (C$_1$-C$_7$)alkyl optionally substituted by (C$_1$-C$_7$)alkyl-O—C(O)—, di-(C$_1$-C$_7$)alkylamino, or hydroxy; or
R$_2$ is aryl-(C$_1$-C$_7$)allyl-, heteroaryl-(C$_1$-C$_7$)alkyl-, heterocyclyl-(C$_1$-C$_7$, wherein said heterocyclyl is optionally substituted by (C$_1$-C$_7$)alkyl; and
R$_3$ is (C$_1$-C$_7$)alkyl; or a pharmaceutically acceptable salt thereof; or an optical isomer thereof; or a mixture of optical isomers.

3. The compound of claim 1, wherein
R$_1$ is (C$_1$-C$_7$)alkoxy, R$_2$ is (C$_1$-C$_7$)alkyl;
R$_3$ is (C$_1$-C$_7$)alkyl; or a pharmaceutically acceptable salt thereof; or an optical isomer thereof; or a mixture of optical isomers.

4. The compound of claim 1, wherein
R$_1$ is (C$_1$-C$_7$)alkoxy;
R$_2$ is (5-9 membered) heteroaryl-(C$_1$-C$_7$)alkyl;
R$_3$ is (C$_1$-C$_7$)alkyl; or a pharmaceutically acceptable salt thereof; or an optical isomer thereof; or a mixture of optical isomers.

5. The compound of formula (II) according to claim 1

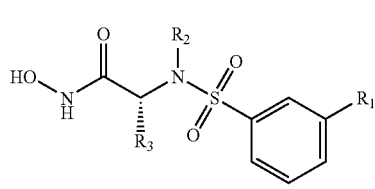

(II)

Wherein
R$_1$ is cyano, (C$_1$-C$_7$)alkyl, R$_4$—O—, (C$_1$-C$_7$)alkyl-NHC(O)—, R$_6$C(O)—, or R$_{10}$—O—(O)—, wherein
R$_4$, R$_6$, and R$_9$ are independently hydrogen, mono- or di-(C$_1$-C$_7$)alkylamino, (C$_1$-C$_7$)alkyl or aryl each of which is optionally substituted by one to five substituents selected from the group consisting of (C$_1$-C$_7$)alkyl, halo, hydroxyl, (C$_1$-C$_7$)alkoxy and aryl;
R$_2$ is (C$_1$-C$_7$)alkyl, which is optionally substituted by one to three substituents selected from the group consisting of (C$_1$-C$_7$)alkyl, hydroxy, aryl, heterocyclyl, heteroaryl, (C$_1$-C$_7$)alkyl-O—C(O)—, di-(C$_1$-C$_7$)alkylamino-C(O)—, wherein each of aryl, heterocyclyl, and heteroaryl is further optionally substituted by (C$_1$-C$_7$)alkyl;
R$_3$ is (C$_1$-C$_7$)alkyl or cycloalkyl;
a pharmaceutically acceptable salt thereof; or an optical isomer thereof; or a mixture of optical isomers.

6. The compound of claim 5, wherein R$_1$ is (C$_1$-C$_7$)alkyl, R$_4$—O—, wherein R$_4$ is (C$_1$-C$_7$)alkyl optionally substituted by one to three halo;
R$_2$ is (C$_1$-C$_7$)alkyl optionally substituted by (C$_1$-C$_7$)alkyl-O—C(O)—, di-(C$_1$-C$_7$)-alkylamino-C(O)—, hydroxy; or
R$_2$ is aryl-(C$_1$-C$_7$)alkyl-, heteroaryl-(C$_1$-C$_7$)alkyl-, heterocyclyl-(C$_1$-C$_7$)alkyl, wherein said heterocyclyl is optionally substituted by (C$_1$-C$_7$)alkyl;
R$_3$ is (C$_1$-C$_7$)alkyl; or
a pharmaceutically acceptable salt thereof; or an optical isomer thereof; or a mixture of optical isomers.

7. The compound of claim 5, wherein
R$_1$ is (C$_1$-C$_7$)alkoxy,
R$_2$ is (C$_1$-C$_7$)alkyl;
R$_3$ is (C$_1$-C$_7$)alkyl; or
a pharmaceutically acceptable salt thereof; or an optical isomer thereof; or a mixture of optical isomers.

8. The compound of claim 5, wherein
R$_1$ is (C$_1$-C$_7$)alkoxy;
R$_2$ is (5-9 membered) heteroaryl-(C$_1$-C$_7$)alkyl;
R$_3$ is (C$_1$-C$_7$)alkyl; or
a pharmaceutically acceptable salt thereof; or an optical isomer thereof; or a mixture of optical isomers.

9. A compound of formula (III) according to claim 1

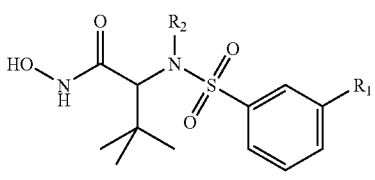

(III)

wherein
R$_1$ is cyano, (C$_1$-C$_7$)alkyl, R$_4$—O—, or R$_6$C(O)—, wherein R and R$_6$ are independently (C$_1$-C$_7$)alkyl or aryl each of which is optionally substituted by one to five substituents selected from the group consisting of $(C_1$-$C_7)$alkyl, halo, hydroxyl, $(C_1$-$C_7)$alkoxy and aryl, $R_2$ is $(C_1$-$C_7)$alkyl, aryl-$(C_1$-$C_7)$alkyl-, or heteroaryl-$(C_1$-$C_7)$alkyl-, (5-9 membered)heterocyclyl-$(C_1$-$C_7)$alkyl, mono-$(C_1$-$C_7)$alkylamino-$(C_1$-$C_7)$alkyl, or di-$(C_1$-$C_7)$alkylamino-$(C_1$-$C_7)$alkyl; or a pharmaceutically acceptable salt thereof; or an optical isomer thereof; or a mixture of optical isomers.

10. The compound of claim 9, wherein $R_1$ is cyano, $(C_1$-$C_7)$alkyl, $R_4$—O—, or $R_6C(O)$—, wherein $R_4$ and $R_6$ are independently $(C_1$-$C_7)$alkyl, phenyl, biphenyl, naphthyl, or tetrahydronaphthyl each of which is optionally substituted by one to five substitutents selected from the group consisting of $(C_1$-$C_7)$alkyl, halo, hydroxyl and $(C_1$-$C_7)$alkoxy; $R_2$ is $(C_1$-$C_7)$alkyl, $(C_6$-$C_{10})$ aryl-$(C_1$-$C_7)$alkyl, or (5-9 membered) heteroaryl-$(C_1$-$C_7)$alkyl, (5-9 membered) heterocyclyl-$(C_1$-$C_7)$ alkyl, or mono-$(C_1$-$C_7)$alkylamino-$(C_1$-$C_7)$alkyl, or di-$(C_1$-$C_7)$alkylamino-$(C_1$-$C_7)$alkyl; or a pharmaceutically acceptable salt thereof; or an optical isomer thereof; or a mixture of optical isomers.

11. A compound of formula (IV) according to claim 9

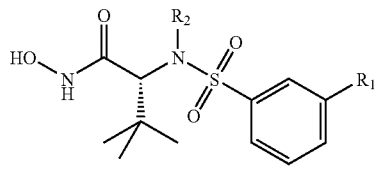

(IV)

Wherein $R_1$ is cyano, $(C_1$-$C_7)$alkyl, $R_4$—O—, or $R_6C(O)$—, wherein $R_4$ and $R_6$ are independently alkyl or aryl each of which is optionally substituted by one to five substituents selected from the group consisting of $(C_1$-$C_7)$alkyl, halo, hydroxyl, $(C_1$-$C_7)$alkoxy and aryl;

$R_2$ is $(C_1$-$C_7)$alkyl, aryl-$(C_1$-$C_7)$alkyl-, or heteroaryl-$(C_1$-$C_7)$alkyl-, (5-9 membered)heterocyclyl-$(C_1$-$C_7)$alkyl, mono-$(C_1$-$C_7)$alkylamino-$(C_1$-$C_7)$alkyl, or di-$(C_1$-$C_7)$alkylamino-$(C_1$-$C_7)$alkyl; or a pharmaceutically acceptable salt thereof; or an optical isomer thereof; or a mixture of optical isomers.

12. The compound of claim 11, wherein $R_1$ is cyano, $(C_1$-$C_7)$alkyl, $R_4$—O—, or $R_6C(O)$—, wherein $R_4$ and $R_6$ are independently $(C_1$-$C_7)$alkyl, phenyl, biphenyl, naphthyl, or tetrahydronaphthyl each of which is optionally substituted by one to five substitutents selected from the group consisting of $(C_1$-$C_7)$alkyl, halo, hydroxyl and $(C_1$-$C_7)$ alkoxy; $R_2$ is $(C_1$-$C_7)$alkyl, $(C_6$-$C_{10})$ aryl-$(C_1$-$C_7)$alkyl, or (5-9 membered) heteroaryl-$(C_1$-$C_7)$alkyl, (5-9 membered) heterocyclyl-$(C_1$-$C_7)$ alkyl, or mono-$(C_1$-$C_7)$alkylamino-$(C_1$-$C_7)$alkyl, or di-$(C_1$-$C_7)$alkylamino-$(C_1$-$C_7)$alkyl; or a pharmaceutically acceptable salt thereof; or an optical isomer thereof; or a mixture of optical isomers.

\* \* \* \* \*